United States Patent [19]
Betsill et al.

[11] Patent Number: 5,785,708
[45] Date of Patent: Jul. 28, 1998

[54] EPILATOR PROBEHOLDER

[75] Inventors: Harry Edwards Betsill, Parkton; Michael Joseph Kovacevich, White Marsh, both of Md.

[73] Assignee: LP Systems Corporation, Richmond Hill, N.Y.

[21] Appl. No.: 531,189

[22] Filed: Sep. 19, 1995

[51] Int. Cl.$^6$ ........................................ A61B 17/41
[52] U.S. Cl. ........................... 606/43; 606/44; 128/908
[58] Field of Search .......................... 606/36, 37, 43, 606/42, 44; 128/908

[56] References Cited

U.S. PATENT DOCUMENTS

| | | | |
|---|---|---|---|
| 4,183,359 | 1/1980 | Husbands | 606/43 |
| 4,224,944 | 9/1980 | Roberts | 606/36 |
| 4,321,926 | 3/1982 | Roge | 606/36 |
| 4,550,728 | 11/1985 | Runyon et al. | 606/36 |
| 4,566,454 | 1/1986 | Mehl et al. | 606/36 |
| 4,821,717 | 4/1989 | Wehrli | 606/44 |
| 5,400,267 | 3/1995 | Denen et al. | 128/908 X |
| 5,432,459 | 7/1995 | Thompson et al. | 128/908 X |

*Primary Examiner*—Robert L. Nasser
*Assistant Examiner*—Ryan Carter
*Attorney, Agent, or Firm*—McAulay Fisher Nisson Goldberg & Kiel, LLP

[57] ABSTRACT

An epilator probeholder for a replaceable, flexible, insulated epilator probe including a length of coaxial cable, and a coaxial capacitor structure for holding the epilator probe. The coaxial capacitor structure has an inner female connector and an outer conductive shell, the coaxial cable inner conductor is connected to the inner female connector for holding the flexible probe, and the coaxial cable outer conductor is connected to the outer conductive shell. The inner female connector is insulated from the outer conductive shell, the other end of the coaxial cable is connected to a standard coaxial connector, and the impedance seen at the input of the standard coaxial connector is standardized.

31 Claims, 4 Drawing Sheets

EPILATOR BLOCK DIAGRAM

FRONT PANEL BLOCK DIAGRAM

EPILATOR RF BOARD BLOCK DIAGRAM

MAIN COMPUTER BLOCK DIAGRAM

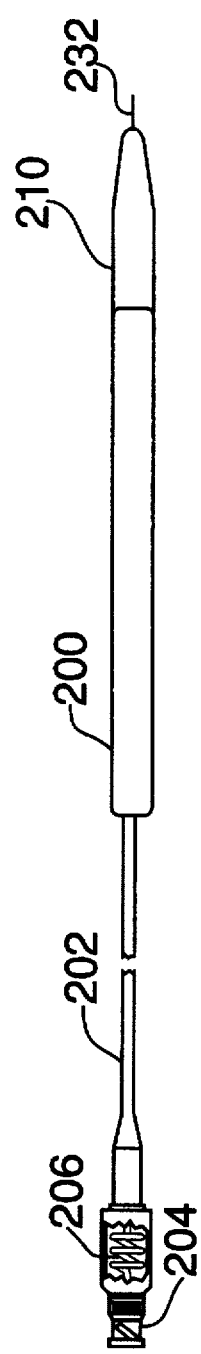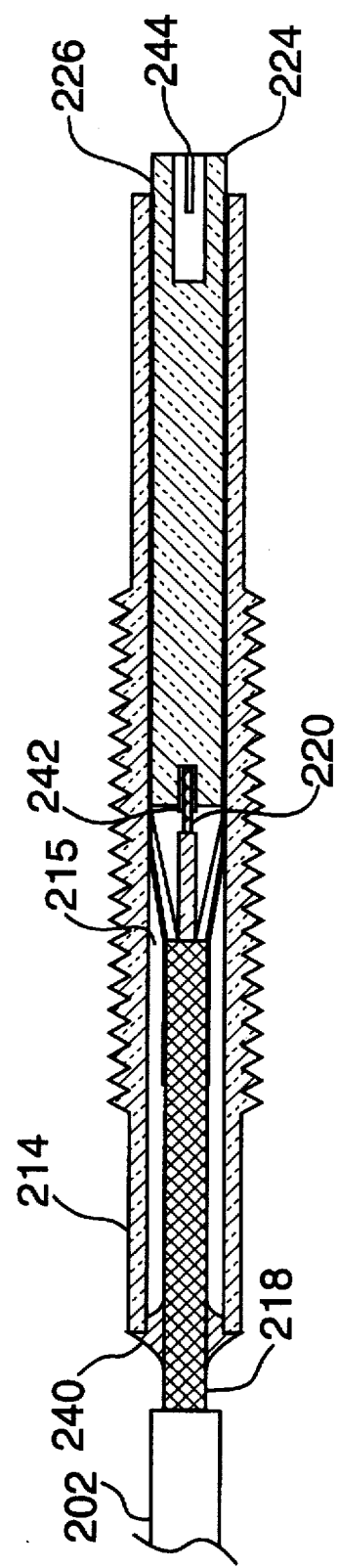

5,785,708

1

EPILATOR PROBEHOLDER

BACKGROUND OF THE INVENTION

1. Field of the Invention

This invention is an improvement over the invention disclosed and claimed in U.S. Pat. No. 4,550,728 to Runyon and Hower, and also relates to a high frequency probe type epilator.

This invention is concerned with an epilation procedure, and a control apparatus and a probeholder used in connection with the epilation procedure.

More particularly, the invention is concerned with precise control of intensity (power level) and timing and dynamic power control based on impedance variation. Variations in the depth of insertion and hair characteristics impact the initial impedance, and the application of power to the follicle results in dynamic impedance changes. The impedance is measured during the pulse and the power is compensated to minimize skin reaction and sensation to the patient.

The invention is also concerned with a novel probeholder.

2. Description of the Prior Act

The prior U.S. Pat. No. 4,550,728, while it also relates to an RF epilator procedure and is also concerned with safety controls, relied on open loop electrical circuit characteristics to select power setting. This resulted in non-linear power variations, as well as, uncontrolled response to variations in impedance during the pulse. The process of RF epilation is performed by inserting an insulated bulbous tipped probe into a follicle and applying a controlled burst of RF energy to the probe. The probe tip concentrates the energy at the germinative portion of the hair (dermal papilla) destroying the follicle's capacity to regenerate itself. Operators, based on their experience, select the timing and intensity of the RF power pulse to be applied. The actual pulse length will not exceed these settings. During the pulse the power delivered is based on the intensity setting selected by the operator as impacted by the inherent response of the circuit to variations of the impedance reflected to the power amplifier output. The impedance as seen at the probe tip varies throughout the duration as a function of skin characteristics, hair size and depth of penetration. During the pulse dynamic changes in the impedance occur as energy is applied to the tissue.

With the prior heretofore known probeholders, an operator using the probeholder became part of the RF load. Different operators presented a different load impedance to the circuit based on their own individual treatment technique. Specifically, as presently understood, the prior heretofore probeholder terminated the coaxial cable center conductor into a large brass tip which accepted the probe. The shield terminated where the center conductor connected to the end of the probeholder allowing RF energy to be coupled to the operator, as well as the patient.

SUMMARY OF THE INVENTION

A primary purpose of any improvement in connection with the electrolysis procedure is to reduce discomfort, prevent scarring and eliminate regrowth. Specifically, as noted heretofore, it is desired to destroy the germinative portion of the hair by treating each follicle just once. This is achieved by concentrating the energy at the tip of the probe at the dermal papilla. Based on operator training and experience and the use of the novel circuitry and novel probeholder of this invention, and the flexible insulated bulbous tipped probe, complete destruction of the germinative portion of the hair takes place, regrowth is eliminated and the

2 follicle itself together with its appendages (sebaceous gland and arrector muscle) are left intact and functioning normally.

The operator, based on experience and observation of the removal characteristics, will select appropriate time and intensity settings to ensure patient comfort and easy removal. Timing can be selected in the range of 1 to 100 milliseconds, and intensity can be selected in the range of 2.5 to 25 watts. The operator then inserts the probe into the follicle, steps on a foot pedal to activate the machine, withdraws the probe and lifts the hair out of the follicle with a forceps.

With the invention described herein, it is possible to record the impedance presented to the power amplifier and power delivered to the matching network during the pulse. The unit is adjusted to a dummy load, equivalent to a nominal hair follicle, to present a nominal impedance of 50 ohms to the amplifier. During a removal, it was observed that the initial impedance is in the range of 50 to 60 ohms. As the power is applied and tissue heating occurs the impedance reduces by approximately 10 percent. The reduction of impedance occurs as a result of softening of the tissue which allows better probe tip contact. If energy is applied too rapidly, the destruction of the tissue at the probe tip results in a rapid increase in impedance. This characteristic, termed as "decoupling", occurs because of the appearance of vapor at the tip. When decoupling occurs energy is no longer efficiently transferred to the base of the hair. If the amplifier is capable of delivering constant power to the probe, the sudden increase in impedance will result in higher voltage being applied to the surrounding tissue. Observation of the decoupling phenomenon led to the erroneous conclusion that the process of removal was complete when decoupling occurred. This was proven by configuring the unit to terminate the pulse when decoupling was sensed. In this mode of operation removals were inconsistent, and pain and skin damage still occurred.

These obervations have led to the conclusion that it is not only necessary to destroy the tissue at the base of the hair, but it is also necessary to soften the sheathing around the hair to allow it to slide out of the follicle. Excessive power after decoupling can result in skin damage, and drying of the hair and/or sheathing which makes removal difficult.

An object of the invention is to accommodate variations in the removal process resulting from variations in hair characteristics and depth of insertion. The operator's experience is still essential to making a proper insertion and in determining proper settings of time and initial power based on quality of removal and patient comfort. To meet this objective, the power during the pulse is adjusted automatically based on the impedance presented at the power amplifier output. The power response to impedance variation, because of the use of the microcomputer, can be programmed to be any response. It has been determined that profiling the power as an inverse square of the measured impedance works well. To perform this task, the microcomputer sets the initial power assuming a nominal 50 ohm impedance. Once the pulse is started, the impedance is measured every millisecond and the power is adjusted accordingly.

FURTHER OBJECTS OF THE INVENTION

Another object of the invention is to ensure consistency between machines. This is accomplished by use of the microcomputer working in conjunction with the RF amplifier circuity. During the alignment and calibration process the performance monitor circuitry is calibrated and constants are saved in the internal battery backed-up RAM. A linearization table is then generated which relates DAC output to power output into a 50 ohm resistive load as measured by the performance monitor. Thus the operator is assured that intensity corresponds from one machine to another.

A further object of the invention is to protect the patient from the inadvertent or misapplication of RF power. This is embodied in the use of the slave microcomputer which independently monitors pulse timing and must cooperate with the main microcomputer to enable the RF amplifier chain. In the idle state between pulses, power supply voltages are removed from the Driver and Final Amplifier stages. The RF oscillator and low level driver are also disabled. Then the linear modulator is set for minimum output.

To activate the chain the RF oscillator is enabled and the slave microcomputer is issued the pulse parameters to be used. The two microcomputers then enable the power supply voltages to the Driver and Final Amplifiers. Two separate outputs from each microcomputer must agree to enable the Driver power supply, and similar outputs are required to enable the Final power supply. Failure of any one of the four outputs from either the master or slave microcomputers will prohibit the generation of a RF pulse. RF power is then enabled by the main microcomputer by enabling the linear modulator and low level driver. This also causes the slave microcomputer to begin independently timing the pulse. Under normal conditions the master computer will terminate the pulse, however, if it should fail, the slave processor will take over and inhibit the output.

A still further object of the invention, as embodied in the improved design of the probeholder is to eliminate the variation of performance dependent on how the operator held the probeholder. As set forth heretofore, this prior design terminated the coaxial cable center conductor into a large brass tip which accepted the probe. The shield terminated where the center conductor connected to the end of the probeholder allowing RF energy to be coupled to the operator, as well as the patient. The operator, therefore, became part of the load. As embodied, the improved probeholder design isolates the operator, so that how the probeholder is held, the angle of the operator's hand, and whether the operator is touching the patient is no longer a significant factor.

Other objects, advantages and the nature of the invention will become apparent from a consideration of the detailed description taken in connection with the following figures of the drawings.

FIG. 5 is a pictorial view of a probeholder according to the invention; and

FIG. 6 is a sectional view of an improved probeholder coaxial termination according to the invention.

DESCRIPTION OF THE PREFERRED EMBODIMENTS

Referring now more particularly to the drawings which illustrate the best mode presently contemplated for carrying out the invention, the microcomputer based epilator apparatus includes a front panel PC board (FPB) 10, an RF power amplifier board (RFB) 12 for driving the novel probeholder 14, and a main computer board (MCB) 16. The unit is powered from either 120 or 230 VAC., 50/60 Hz as derived from the power supply interface 18.

Figure 1:
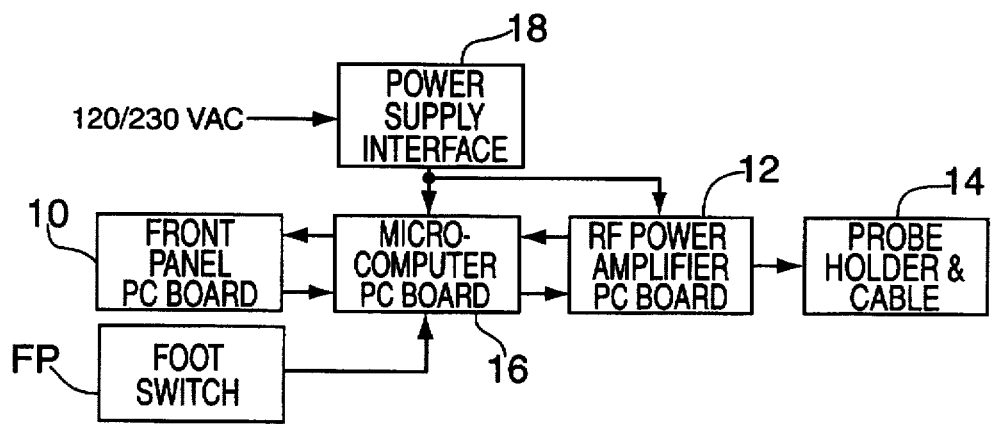
FIG. 1 is a block diagram of a microcomputer based epilator circuitry and apparatus according to the invention.
Figure 2:
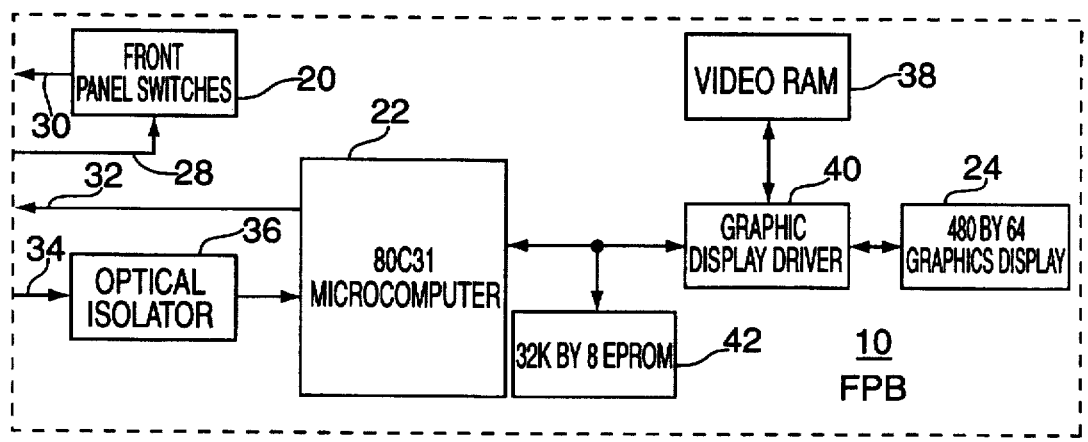
FIG. 2 is a front panel board and includes a microcomputer for driving the graphics display and push button switches for operator input.

Front panel board 10, as shown in detail in FIG. 2, is devoted to operator interface and includes front panel switches 20, an 80C31 microcomputer 22, graphics display driver 40, and a 480 by 64 pixel graphics LCD display 24. The main computer board 16 interfaces to the switches via inputs 28 and outputs 30.

The graphics display interface consists of microcomputer 22, an 80C31, graphics display driver IC 40, and video RAM 38. The graphics display driver IC 40 directly interfaces to the graphics display 24. Program memory for microcomputer 22 is contained in EPROM 42 which also contains custom character generation tables for the graphics display. Display commands are sent by the main microcomputer 16 over an optically isolated serial link comprising line 34 and optical isolator 36 to the microcomputer 22. A display confidence indication is provided via line 32.

The operator selects the intensity and timing for the pulse to be applied to the patient by activation of the push button front panel switches 20. Readback of selected timing and intensity is provided by graphics display 24. Additional features supported by the front panel provide for treatment and area timing, as well as, a time of day clock.

Figure 3:
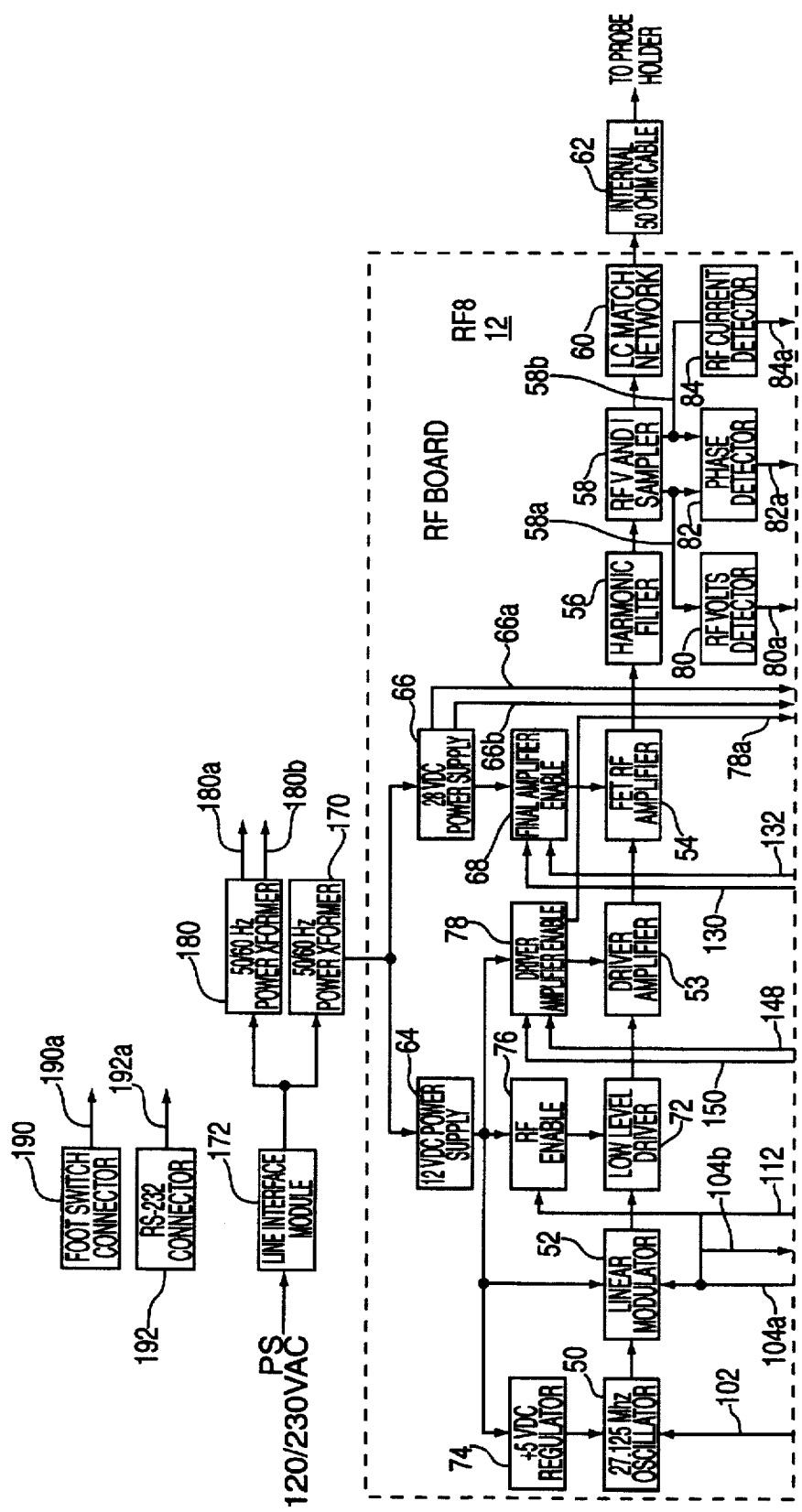
FIG. 3 is an RF board including power supply components, RF amplifier chain, performance monitor, and matching network for driving the probeholder.

The RF 12 as shown in FIG. 3 contains the circuitry to generate a linearly variable RF pulse with a maximum power output of 25 watts into an impedance of 50 ohms. The major components of the RF subsystem RFB 12 are a 27.120 MHz crystal oscillator 50, linear modulator 52, a low level driver 72, 2 watt driver stage 53, FET final RF amplifier 54, harmonic filter 56, RF V and I sampler 58, and an LC matching network 60. The board also contains the power supply rectifiers, filters and regulators 64 to develop a 12 VDC for the low level RF circuitry, and power supply rectifiers, filters and regulators 66 to develop 28 VDC to power final RF amplifier 54. A separate 5 VDC regulator 74 provides power for the oscillator 50. RF enable 76 controls application of power to the low level RF circuits. The driver amplifier enable 78 requires two inputs 148 and 150 from the main computer board 16 (FIG. 4) to be in the active state before power is applied to the driver stages. Similarly, final amplifier enable 68 requires inputs 130 and 132 to be satisfied before power can be applied to the final amplifier 54. Independent logic signals 102 and 112 from the main computer board 16 (FIG. 4) enable the oscillator 50 and low level driver 72.

The RF final amplifier 54 is a N-channel FET operating as broadband Class B linear amplifier. An output loading of 11 ohms is realized by a 4 to 1 broadband transformer that drives harmonic filter 56. The harmonic filter 56 is a seven pole low pass filter tapered to present 44 ohms at its input when loaded with a nominal 50 ohm output. The nominal power output is 25 watts at the output of the harmonic filter. Class B bias is provided by an adjustable regulator.

Figure 4:
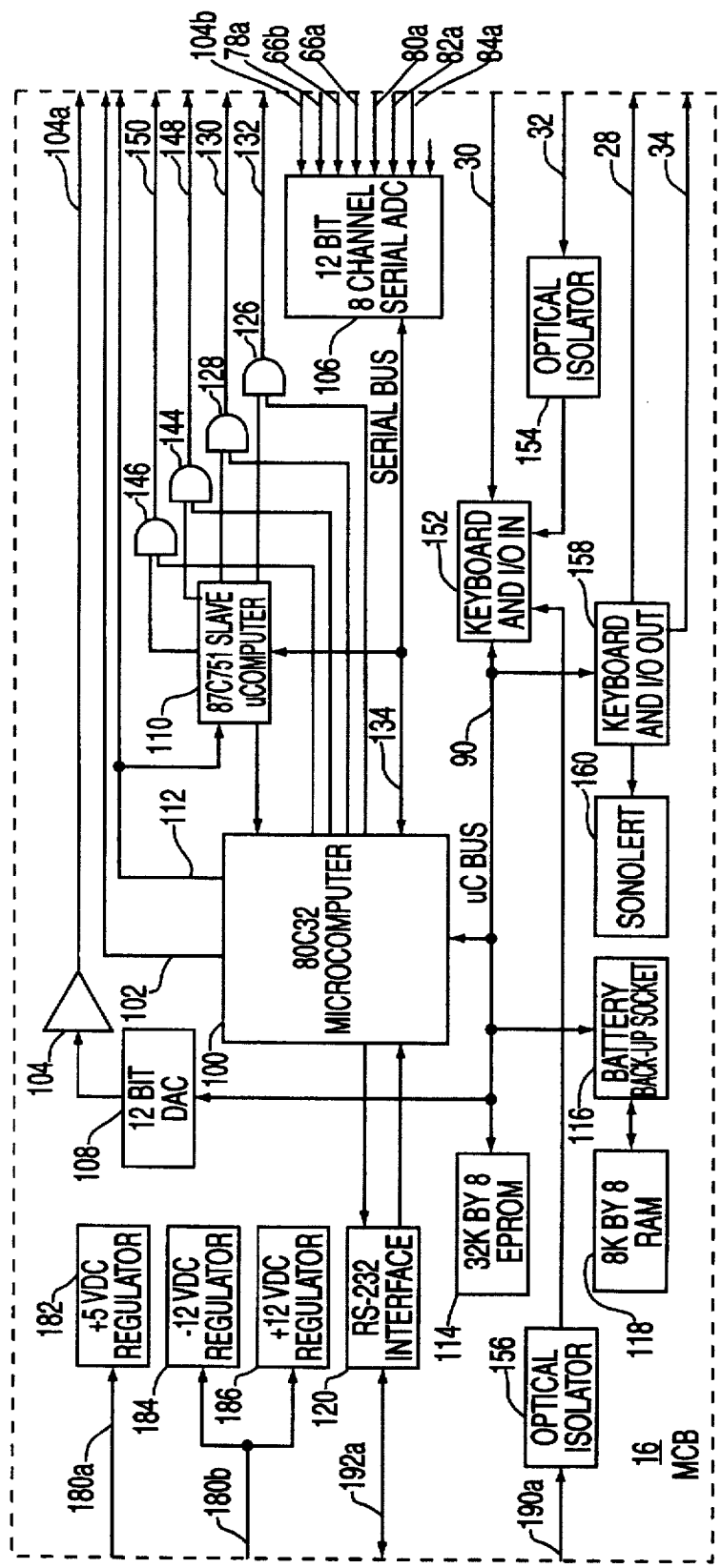
FIG. 4 is a main computer board for controlling and monitoring the RF board, and interfacing to the operator via the front panel board.

Outputs 66a and 66b from the 28 VDC power supply 66 are 0 to 5 volt analog signals proportional to final voltage and current which input to the ADC located on the main computer board 16 (FIG. 4). Output 78a from the driver enable circuitry 78 provides an analog readback to the ADC located on the main computer board 16 (FIG. 4) proportional to driver DC voltage.

RF V and I sampler 58 provides RF voltages proportional to load voltage 58a and load current 58b. These outputs separately drive linear detectors 80 and 84 to derive outputs 80a and 84a which are 0 to 5 volt signals proportional to the load voltage and current, respectively. Signals 58a and 58b are also used to drive a phase detector 82 which produces an output 82a from 0 to 5 volts, centered about 2.5 volts, proportional to the sine of the phase angle between the two inputs. The main computer samples these voltages to compute power output and the magnitude and phase of the load impedance.

The LC matching network 60 is necessary to transform the impedance reflected from the probe tip through the probeholder cable and the internal 50 ohm cable 62 to a nominal 50 ohms at its input. Because the total cable length of the probeholder and internal cabling approximates a quarter wavelength, the high impedance at the probe tip is transformed to a low impedance at the output of the matching network.

Referring now to FIG. 4, the main computer board 16 provides the intelligence to monitor the RF subsystem 12 and interface to the operator via the front panel 10. The main computer 100 is an 80C32 microcomputer operating with external program memory as provided by EPROM 114 which resides on the microcomputer bus 90. The microcomputer bus 90 also interfaces to data memory RAM 118 via a battery back-up socket 116, a 12 bit parallel DAC 108, and keyboard and I/O circuits 152 and 158.

Battery back-up to the RAM 118 is essential to maintaining calibration constants and linearization table needed for normal system operation during periods when power is not available. In addition, the battery back-up socket 116 provides a time of day function.

The microcomputer 100 scans the front panel switches as a 4by 4 keypad using four of the eight outputs available from Keyboard and I/O Out bus latch 158. Readback of the keys is provided by four of the eight inputs Keyboard and I/O In circuit 152. One of the remaining outputs from 158 are used to enable the sonalert 160 which provides audible feedback to the operator that an RF pulse has been generated. Another of the outputs from 158 provides a high speed, start-stop, serial data stream to the front panel display microcomputer board 10 via line 34. A confidence read back from front panel display microcomputer board 10 is provided by line 32 driving the optical isolator 154. This signal is polled by the microcomputer 100 via one of the inputs of 152.

The foot switch FP, via connector 190 over line 190a, interfaces to optical insolator 156, and is used by the operator to initiate a pulse. This signal is sensed by the microcomputer 100 using one of the inputs of 152.

The microcomputer 100 sets the required power level via the 12 bit DAC (digital-to-analog converter) 108 over the microcomputer bus 90. The DAC output is buffered by amplifier 104 to drive the linear modulator 52 via line 104a.

A high speed serial bus 134, under the control of microcomputer 100, interfaces to the slave microcomputer 110 and the 8 channel, 12 bit ADC 106. The purpose of the 87C751 slave microcomputer 110 is to monitor the timing of the RF pulse and cooperate with the main microcomputer 100 in the generation of the RF pulse. To perform the function, it is necessary for the main microcomputer 100 to communicate the pulse length and pulse commands to the slave microcomputer 110.

Four direct port I/O pins from each microcomputer, 100 and 110, must agree to enable an RF pulse. The four signals from each microcomputer drive separate AND gates 126, 128,144 and 146. Failure of any one of the eight signals will prohibit generation of a RF pulse, or terminate a pulse in process. The outputs of AND gate 126 and 128 are used to control power supply voltage to the final amplifier via final amplifier enable 68 over lines 130 and 132. Likewise, AND gates 144 and 146 enable the driver power supply voltage over lines 148 and 150. Microcomputer output 112 is used to enable the low level driver 72, and to trigger the slave microcomputer 110 which starts the independent timer function of the slave microcomputer.

The serial 8 channel, 12 bit ADC 106 (analog-to-digital converter) is read by microcomputer 100 to monitor RF pulse parameters such as RF voltage 80a, RF current 84a and the phase difference between RF voltage and current 82a. In addition, final voltage 66a, final current 66b, and driver voltage 78a are measured. As a confidence check, the DAC output 104b can be read via the ADC 106 to confirm the presence of the RF board. The power output and load impedance can be calculated from the three RF parameters measured.

During a pulse, the three RF parameters, voltage, current, and phase, and final voltage and final current are measured every millisecond and saved in RAM. The main computer, after taking the readings, computes the magnitude of the load impedance and outputs a new DAC value corresponding to the power appropriate for that impedance. The RS-232 interface 120, along with connector 192 and signal lines 192a, is used in conjunction with an external IBM-PC compatible computer to control and monitor the epilator performance. In the calibration process, calibration constants are derived for the RF detectors 80, 82 and 84, as well as, the final voltage and current samplers. These constants are then downloaded to the epilator and retained in RAM 118. The last step in unit calibration is generation of a level calibration table. The purpose of the level calibration table is to allow interpolation of desired intensity setting, selected by the operator as a number from 10 to 99, to a corresponding DAC value. Because the calibration constants and level table are essential to normal operation checksums are maintained which allow validation of the table values.

The board contains the rectifiers, filter capacitors and regulators to develop +5 VDC 182, and +12 VDC 186 and −12 VDC 184. The +5 VDC is used for the logic circuits while the +12 VDC and −12 VDC are used to power the low level analog circuits. Isolation between the analog and digital supplies is provided by separate secondary windings outputs 180a and 180b of transformer 180.

The case mounted parts as shown in FIG. 3 include two power transformers 170 and 180 , a line interface module 172 , a foot switch connector 190, and an RS-232 interface connector 192. A power source PS is selectable to be 120/230 VAC, 50/60 Hz. Separate power transformers 170 and 180 are essential to maintaining isolation between the high power RF circuitry and the low level analog and digital circuitry.

The probeholder assembly represents one of the major changes in the epilator. Prior art probeholder designs made the operator a part of the RF path because of a large brass piece designed to hold the probe. Since this piece was connected to the cable center conductor, significant capacity coupling to the operator resulted in a circuit such that the operator was in parallel with the load presented by the patient. The actual loading of the probe was, thus, variable depending on how the operator held the probeholder, whether the operator was touching the patient, as well as, the angle of the operator's hand relative to the patient.

To isolate the operator, the probeholder was redesigned to extend the coaxial structure to the end of the probeholder. In the process, intentional capacity of approximately 30 pF was added to the end of the coaxial cable. The purpose of the added capacity is to limit the RF voltage at the end of the cable when the probe is not loaded.

Referring to FIG. 5 which shows a novel epilator probeholder 14 comprising a BNC connector and housing 204, a coaxial cable 202, handle 200, protective tip 210, and replaceable probe 232. An adjustable coil 206, located in BNC housing 204, provides for a means for standardizing the probeholders to present a substantially equivalent impedance at the BNC connector when terminated in to a standard load.

Referring to FIG. 6 which shows the internal construction of the cable termination and probe interface. The inner conductor 220 of the coaxial cable is soldered 242 to one end of the cylindrical Beryllium Copper female connector 224. The other end of 224 is designed to accept and hold the probe 232 in opening 244. A layer of Kapton® is used to insulate the inner conductor 220 and brass piece 224. A controlled coaxial capacitor is then formed by adding a layer of copper tape 215 over the Kapton® tape and outer conductor 218 of the coaxial cable. The copper tape is soldered to the outer conductor. The completed assembly is positioned in the threaded sleeve 214 and solder 240 is applied to the outer conductor and sleeve.

The nylon handle 200 threads onto 214 and protects the cable 202. Protective tip 210 threads on the other end of 214, and is removable to allow the operator to change the probe 232.

The actual circuit implementation establishes a preferred embodiment of the invention. The improvements are: 1) the ability to profile the power output based on the measured impedance during the removal pulse; 2) improved protection of the patient by use of the slave microcomputer; and 3) the structure of the probeholder to add capacity and eliminate stray capacity effects produced by the operator holding the probeholder. The features realized by using the microcomputer according to the invention include complete control and monitoring of the RF pulse which allows, in conjunction with an external computer, analysis of the removal characteristics of each pulse.

What is claimed is:

1. An epilator probeholder for a replaceable, flexible, insulated epilator probe comprising:

a length of coaxial cable having an inner conductor and an outer conductor;

a coaxial capacitor structure for holding said replaceable, flexible, insulated epilator probe comprising an inner female connector and an outer conductive shell;

means connecting said coaxial cable inner conductor to said inner female connector for holding said flexible probe, and means for connecting said outer conductor to said outer conductive shell;

means for insulating said inner female connector from said outer conductive shell;

means for connecting an end of said coaxial cable to a standard coaxial connector; and a connector housing for housing said standard coaxial connector, said housing including means for standardizing the impedance seen at the input of said standard coaxial connector.

2. The epilator probeholder of claim 1, wherein said means for connecting said coaxial cable outer conductor includes a first covering for covering said insulating means with a conductive tape connected to said outer conductor prior to connecting to said outer conductive shell.

3. The epilator probeholder of claim 1, where said inner female connector is beryllium copper.

4. The epilator probeholder of claim 2, wherein said insulating means is a layer of insulating tape, and said conductive tape is copper.

5. The epilator probeholder of claim 1, wherein said impedance standardizing means comprises an adjustable inductor in said housing.

6. The epilator probeholder of claim 1, including a handle threaded onto said outer conductive shell.

7. The epilator probeholder of claim 3, including means soldering said coaxial cable inner conductor to said inner female connector.

8. The epilator probeholder of claim 7, wherein said insulating means is a layer of insulating tape for covering said coaxial cable inner conductor and said inner female connector.

9. An epilator probeholder for a replaceable, flexible, insulated epilator probe comprising:

a length of coaxial cable having an inner conductor and an outer conductor;

a coaxial capacitor structure for holding said replaceable, flexible, insulated epilator probe, said coaxial capacitor structure comprising an inner female connector and an outer conductive shell;

means connecting said coaxial cable inner conductor to said inner female connector for holding said flexible probe, and means connecting said coaxial cable outer conductor to said outer conductive shell;

means for insulating said inner female connector from said outer conductive shell;

means for connecting an end of said coaxial cable to a standard coaxial connector; and a handle threaded onto said outer conductive shell.

10. The epilator probeholder of claim 9, including means for standardizing the impedance seen at the input of said standard coaxial connector.

11. The epilator probeholder of claim 9, including a first covering for covering said insulating means with a conductive tape connected to said coaxial cable outer conductor prior to connecting to said outer conductive shell.

12. The epilator probeholder of claim 11, wherein said inner female connector is beryllium copper.

13. The epilator probeholder of claim 11, wherein said insulating means is a layer of insulating tape, and said conductive tape is copper.

14. The epilator probeholder of claim 10, wherein said impedance standardizing means comprises an adjustable inductor in said housing.

15. The epilator probeholder of claim 14, including a layer of insulating tape for insulating said coaxial cable inner conductor and said inner female connector.

16. The epilator probeholder of claim 9, including solder applied to said coaxial cable outer conductor, and said outer conductive shell.

17. The epilator probeholder of claim 9, including a connector housing for housing said standard coaxial connector, said housing including means for standardizing the impedance seen at the input of said standard coaxial connector.

18. The epilator probeholder of claim 9, where said inner female connector is beryllium copper.

19. The epilator probeholder of claim 9, including means soldering said coaxial cable inner conductor to said inner female connector.

20. The epilator probeholder of claim 9, including impedance standardizing means for standardizing the impedance seen at the input of said standard coaxial connector comprising an adjustable inductor in said housing.

21. The epilator probeholder for a replaceable, flexible, insulated epilator probe comprising:

a length of coaxial cable having an inner conductor and an outer conductor;

a coaxial capacitor structure for holding said replaceable, flexible, insulated epilator probe, said coaxial capacitor structure comprising an inner female connector and an outer conductive shell;

means connecting said coaxial cable inner conductor to said inner female connector for holding said flexible probe, and means connecting said coaxial cable outer conductor to said outer conductive shell;

means for insulating said inner female connector from said outer conductive shell;

means for connecting an end of said coaxial cable to a standard coaxial connector; and means for standardizing the impedance seen at the input of said standard coaxial connector.

22. The epilator probeholder of claim 9, wherein said insulating means is a layer of insulating tape for covering said coaxial cable inner conductor and said inner female connector.

23. The epilator probeholder of claim 21, including a handle threaded onto said outer conductive shell.

24. The epilator probeholder of claim 23, including solder applied to said coaxial cable outer conductor and said outer conductive shell.

25. The epilator probeholder of claim 21, including a first covering for covering said insulating means with a conductive tape connected to said coaxial cable outer conductor prior to connecting to said outer conductive shell.

26. The epilator probeholder of claim 21, wherein said female connector is beryllium copper.

27. The epilator probeholder of claim 21, wherein said insulating means is a layer of insulating tape, and said conductive tape is copper.

28. The epilator probeholder of claim 21, wherein said impedance standardizing means comprises an adjustable inductor in said housing.

29. The epilator probeholder of claim 21, wherein said impedance standardizing means comprises an adjustable inductor in said housing.

30. The epilator probeholder of claim 21, including handle threaded onto said outer conductive shell.

31. The epilator probeholder of claim 29, including a handle threaded onto said outer conductive shell.

* * * * *